United States Patent [19]

Fayter, Jr.

[11] Patent Number: 4,713,478

[45] Date of Patent: * Dec. 15, 1987

[54] PROCESS FOR THE PREPARATION OF DIALKYL 2-VINYLCYCLOPROPANE-1,1-DICARBOXYLATES

[75] Inventor: Richard G. Fayter, Jr., Fairfield, Ohio

[73] Assignee: National Distillers and Chemical Corporation, New York, N.Y.

[*] Notice: The portion of the term of this patent subsequent to Dec. 15, 2004 has been disclaimed.

[21] Appl. No.: 936,001

[22] Filed: Nov. 28, 1986

[51] Int. Cl.[4] ............................................ C07C 69/743
[52] U.S. Cl. .................................................... 560/124
[58] Field of Search ........................................ 560/124

[56] References Cited

U.S. PATENT DOCUMENTS

| | | | |
|---|---|---|---|
| 4,252,739 | 2/1981 | Fayter | 560/124 |
| 4,321,406 | 3/1982 | Fayter | 560/124 |
| 4,328,168 | 5/1982 | Fayter | 560/124 |

*Primary Examiner*—Michael L. Shippen
*Attorney, Agent, or Firm*—Kenneth D. Tremain; Gerald A. Baracka

[57] ABSTRACT

This invention relates to the preparation of dialkyl-2-vinylcyclopropane-1,1-dicarboxylates involving the addition of an alcoholic metallic alkoxide to an organic solution of a 1,4-dihalobutene-2 and a malonic ester.

6 Claims, No Drawings

PROCESS FOR THE PREPARATION OF DIALKYL 2-VINYLCYCLOPROPANE-1,1-DICARBOXYLATES

BACKGROUND OF THE INVENTION

G. S. Skinner, et al. first reported the condensation of 1,4-dihalo-2-butene and diethyl malonate in J. Am. Chem. Soc., 72, 1648(1950). The condensation was conducted under anhydrous conditions by reacting the dihalide with the pre-formed disodio anion of the malonic ester in an attempt to synthesize spirocyclopentane-1,5-barbiturates. Kierstead, et al. (J. Chem. Soc., 1952, 3610-21 and J. Chem. Soc., 1953, 1799) reported the preparation of diethyl 2-vinylcyclopropane-1,1-dicarboxylate by the condensation of 1,4-dibromo-2-butene and ethyl sodiomalonate and observed that continual attack by malonate and anion on the 2-vinylcyclopropane derivative produced side products, one of which was 2-vinylbutane-1,1,4,4-tetracarboxylate. Kierstead, et al. also extended the general reaction to ethyl cyanoacetate and ethyl acetoacetate to obtain the corresponding 2-vinylcyclopropane derivatives. In an attempt to develop a new synthetic route for the preparation of the cyclopentane counterparts by deoxyribonucleosides, Murdock, et al. in J. Amer. Chem. Soc., 27, 2395 (1962) reported condensing cis-1,4-dichlorobutene-2 with sodiomalonic ester under anhydrous conditions as the first step in their reaction sequence.

With all of the above reactions, as well as in other reports dealing with the condensation of malonic esters with 1,4-dihalo-2-butenes, e.g. Birch, et al., J. Org. Chem. 23, 1390 (1958); Schmid, et al., J. Org. Chem. 32, 254 (1967); Stewart, et al., J. Org. Chem., 34, 8 (1969), the metal alkoxide and malonic ester were prereacted to first form the corresponding sodiomalonate anion, which was then very slowly added to the dihalobutene. This procedure was considered essential for the successful conduct of the reaction and to optimize the yield of the vinylcyclopropane dicarboxylate. The dihalo compound was not combined directly with the alcoholic caustic to avoid ether by-product formation since this is a well known and widely used procedure (Williamson synthesis) for the preparation of ethers. By adding the malonate anion to the dihalobutene and carefully controlling the rate of this addition, it was believed that linear diaddition products formed by either continued attack on the vinylcyclopropane product by malonate anion or reaction of both the halogens on a single molecule would be minimized. Strictly anhydrous conditions were employed throughout the entire reaction procedure, i.e. during the formation of the anion and the addition of the anion to the dihalobutene, since it is generally accepted that for malonate and acetoacetic ester condensations the presence of water is detrimental (Practical Organic Chemistry, A. I. Vogel, 3rd Ed., Longmans, Green and Co., Ltd., London (1967) pp. 481-486). Even as late as 1970 the classical procedure first developed by Skinner and coworkers was still being used as evidenced by the report of Den Besten, et al. (J. Chem. Eng. Data, 15, 453 (1970)) who prepared diethyl 2-vinylcyclopropane-1,1-dicarboxylate for subsequent thermal decomposition.

In view of the complex state of the reagents, the requirement to operate under strictly anhydrous conditions and the necessity for a sophisticated reaction vessel to carry out the detailed addition, it has heretofore not been practical to prepare vinylcyclopropane derivatives on a commercial scale via such condensation reactions.

U.S. Pat. Nos. 4,328,168 and 4,328,169 inter alia, describe improved processes for the preparation of vinylcyclopropane derivatives. These processes are adaptable to commercial operation and involve reacting, in a fluid state, an alkylating agent, e.g. 1,4-dichlorobutene-2, and an activated methylene compound, e.g. dimethyl malonate, in the presence, respectively, of a cyclic polyether compound or an alkylene oxide derivative and an alkali metal compound. A wide variety of cyclopropane derivatives are readily obtained by these processes.

Another process which has met with favor in overcoming the disadvantages of the earlier literature processes is the phase-transfer-catalyzed synthesis of vinylcyclopropane derivatives described in U.S. Pat. No. 4,252,739, among others, and which involves reacting an alkylating agent, e.g. 1-4-dichlorobutene-2, and an activated methylene compound, e.g. a lower alkyl malonate in the presence of an onium compound, an alkali metal compound and water. While this process works well with certain lower alkyl esters of 2-vinylcyclopropane-1,1-dicarboxylate, for example the ethyl and higher esters, it produces lower yields of the order of <10% when dimethyl 2-vinylcyclopropane-1,1-dicarboxylate is sought to be obtained. It appears that the phase-transfer process when directed to the synthesis of the dimethyl ester produces low yields due to ester saponification which is apparently competitive with the condensation reaction in the presence of methyl esters but which saponification is insignificant with the ethyl and higher esters.

It would be highly desirable, therefore, if an improved process for the preparation of di lower alkyl 2-vinylcyclopropane-1,1-dicarboxylates by the reaction of 1,4-dihalobutenes and malonic esters were available which did not possess the drawbacks of the prior art processes. It would also be desirable if it were possible to eliminate the need for conducting the process in a stepwise manner, i.e., preforming the anion, and if the need for maintaining strictly anhydrous conditions could be eliminated and if the yield of the desired product could be increaseed, the process would have even greater utility. These and other advantages are realized by the improved process of this invention.

It is, therefore, an object of the present invention to provide an improved process for the production of di lower alkyl-2-vinylcyclopropane-1,1-dicarboxylates by the reaction of 1,4-dihalobutenes and malonic esters which does not have the drawbacks associated with the prior art processes.

It is a further object of the present invention to provide a process of preparing high yields of dimethyl 2-vinylcyclopropane-1,1-dicarboxylate without the attendant saponification of the ester with resulting low yields of the desired product as has been observed in the prior art processes.

These and other objects of the present invention are readily achieved by the novel process hereinafter described.

BRIEF SUMMARY OF THE INVENTION

The present invention is based upon the discovery that high yields, of the order of 75% or higher, of di lower alkyl-2-vinylcyclopropane-1,1-dicarboxylates can be readily obtained by the addition of a alcoholic solution of a suitable metallic alkoxide to a solution of a malonic ester, and a 1,4-dihalobutene-2 in a lower alcohol solvent. The reaction is exothermic but is easily controlled by alcohol reflux. Workup consists of filtration, neutralization with a mineral acid, a second filtration, removal of solvent under vacuum and a final vacuum distillation. Crude yields are consistently 80–85% with distilled yields in the range of 75–80%.

DETAILED DESCRIPTION OF THE INVENTION

The process of the present invention, therefore, relates to the preparation of di lower alkyl-2-vinylcyclopropane-1,1-dicarboxylates and more particularly is concerned with the preparation of such compounds by a novel process comprising the addition of an alcoholic metallic alkoxide to a solution of an olefin, for example 1,4-dihalobutene-2 and a malonic ester. The reaction is preferably carried out in the presence of an inert organic solvent, e.g. a lower alcohol, at reflux temperatures. Preferably the procedure involves the rapid addition of 25% methanolic sodium methoxide to a solution of 1,4-dichlorbutene-2 and dimethyl malonate in a minimum amount of methanol. The reaction temperature is maintained at 65°–70° C. by methanol reflux and maintenance of a low temperature by the slow addition of methoxide is not needed. After the reaction is complete, the mixture is vacuum filtered, neutralized preferably with concentrated hydrochloric acid and filtered a second time to complete the removal of all salts. The solvent is then removed under vacuum to produce a yield of crude product of 80–85%. Final vacuum distillation produces a product of 75–80% yield.

Suitable organic solvents for the reaction include the lower alcohols, for example, methanol, ethanol, propanol, and the like, methanol being preferred for ease of handling.

Suitable metallic alkoxides include, for example, sodium or potassium methoxide, ethoxide, propoxide, butoxide, and the like. Again, a methanolic sodium methoxide solution is preferred.

The reaction may be neutralized with any strong mineral acid, e.g. sulfuric acid, hydrochloric acid, etc.

Suitable halogenated olefins for use in the present invention include:
1,4-dichlorobutene-2; 1,4-dibromobutene-2;
1-bromo-4-chlorobutene-2;
1,4-dichloro-2-methylbutene-2; 1,4-dibromo-2-methylbutene-2;
1,4-dichloro-2,3-dimethylbutene-2;
1,4-dibromo-2,3-dimethylbutene-2;
1,4-dichloropentene-2; 1,4-dibromopentene-2; 1,4-dichloro-4-methylpentene-2; and
1,4-dibromo-4-methylpentene-2;

1,4-Dichloro- and 1,4-dibromobutene-2 are particularly useful for the present process in view of their commercial availability, reactivity and ability to yield highly useful vinylcyclopropane derivatives with minimal undesirable by-product formation.

Particularly preferred 1,4-dihalobutene-2 olefins for use in the present process are the trans-1,4-dichlorobutene-2 and trans-1,4-dibromobutene-2 obtained by the isomerization process described in our copending application entitled EFFICIENT CIS-TO-TRANS ISOMERIZATION OF 1,4-DIHALOBUTENE-2 filed concurrently herewith. As therein described a commercial mixture of 1,4-dichlorobutene-2 (77/23) trans/cis can be isomerized to yield a high trans (>93%) mixture by catalytic isomerization of the olefin by either anhydrous hydrogen bromide or 2-mercaptoethanol initiated by 2,2'-azobisisobutyronitrile or ultraviolet light. Trans-1,4-dichlorobutene-2 is the preferred olefin in the vinylcyclopropane synthesis to prevent formation of cyclopentene derivatives. As described in the aforesaid copending application, 1,4-dibromobutene-2 may be readily isomerized in the same fashion to produce good yields of the desired trans isomer.

Suitable malonic esters for use in the present process are the lower alkyl malonates, such as dimethyl malonate, diethyl malonate, dibutylmalonate, disopropyl malonate, ethyl(N,N-dimethyl-2-aminoethyl)malonate, and di(N,N-dimethyl-2-aminoethyl)malonate and the like, dimethyl malonate being preferred because of its ready availability.

The invention will be described in greater detail in conjunction with the following specific examples in which the parts are by weight unless otherwise specified.

EXAMPLE 1

Dimethyl 2-Vinylcyclopropane-1,1-dicarboxylate
(Comparative example—not part of the present invention)

Sodium methoxide (108.02 g, 2.0 moles) 25% in MeOH was added slowly (~2.25 hrs.) to dimethyl malonate (132.12 g, 1.0 mole) in a heated and stirred flask having a bottom opening; 200 mL additional MeOH was required to maintain fluidity of the slurry. The sodiomalonate was then added (~30 min.) through the bottom opening to 1,4-dichlorobutene-2 (125 g, 1.0 mole) in a second heated and stirred flask. The mixture was heated at reflux ~4.5 hours, cooled, and vacuum filtered. The clear filtrate was then concentrated under vacuum at which point additional salts precipitated. An attempted second filtration was unsuccessful due to the slimy cake, and the salts were finally removed by centrifuging to give 146 g of crude product. Vacuum distillation (60°/0.4 mm–90°/0.55 mm) gave a small forecut, 87.6 g of product (47.6% yield), and 44.5 g of residue.

EXAMPLE 2

Dimethyl 2-Vinylcyclopropane-1,1-dicarboxylate

Sodium methoxide (108.02 g, 2.0 moles) 25% in MeOH was added in 40 minutes to dimethyl malonate (132.12 g, 1.0 mole), 1,4-dichlorobutene-2 (150 g, 1.2 moles), and 50 mL MeOH and allowed to stir at ambient temperature overnight. The mixture was vacuum filtered, neutralized with concentrated HCl to 3.5–4.0 pH, and filtered a second time. Solvent was then removed under vacuum to give 194.8 g of light yellow crude product. Vacuum distillation (55°/0.25 mm–72°/0.4 mm) with 0.064 g of hydroquinone added gave 142.5 g of product (77.4% yield) and 30.4 g of residue.

EXAMPLE 3

Isomerization of Dichlorobutene with 2-Mercaptoethanol and 2,2'-Azobisisobutyronitrile To 10 mL of 1,4-dichlorobutene-2 was added 0.5 mL of 2-mercaptoethanol (7.5 mole % based on dichlorobutene and 0.15 g of 2,2'-azobisisobutyronitrile (0.97 mole %). The reaction was then stirred at 80° C. with the following results:
0 minutes: 80.5/19.2 trans/cis
15 minutes: 88.9/ 8.5 trans/cis
30 minutes: 91.0/ 6.7 trans/cis

EXAMPLE 4

Isomerization of Dichlorobutene with HBr and UV Light

Approximately 100 mL of 1,4-dichlorobutene-2 was saturated with anhydrous HBr by subsurface introduction through a fritted glass gas dispersion tube. HBr addition was terminated when persistent fumes were visible above the liquid surface. The mixture was then stirred at ambient temperature while being irradiated with a Pen-Ray* lamp with the following results:

0 minutes: 76.6/22.9 trans/cis
5 minutes: 90.9/ 5.4 trans/cis
10 minutes: 90.4/ 5.1 trans/cis

* 2.5 watts output with 80-90% of radiation at 253.7 nm.

EXAMPLE 5

The procedure of Example 2 was followed except that trans-1,4-dichlorobutene-2 as obtained by the procedure of Example 3 was condensed with dimethyl malonate. High yields of dimethyl 2-vinylcyclopropane-1,1-dicarboxylate of high purity were obtained.

EXAMPLE 6

The procedure of Example 2 was followed except that trans-1,4-dichlorobutene-2 as obtained by the procedure of Example 4 was condensed with dimethyl malonate. High yields of dimethyl 2-vinylcyclopropane-1,1-dicarboxylate of high purity were obtained.

What is claimed is:

1. A process of preparing dialkyl 2-vinylcyclopropane-1,1-dicarboxylates which comprises condensing a di lower alkyl malonic ester with a 1,4-dihalobutene-2 in the presence of an alcoholic solution of a metallic alkoxide and recovering the dialkyl 2-vinylcyclopropane-1,1dicarboxylate so produced.

2. The process according to claim 1 in which the malonic ester is dimethyl malonate.

3. The process according to claim 1 in which the 1,4-dihalobutene-2 is 1,4-dichlorobutene-2.

4. The process according to claim 1 in which the 1,4-dihalobutene-2 is 1,4-dibromobutene-2.

5. The process according to claim 1 in which the 1,4-dihalobutene-2 is essentially trans-1,4-dichlorobutene-2.

6. The process according to claim 5 in which the trans-1,4-dichlorobutene-2 is the isomerized product from a trans/cis mixture of 1,4-dichlorobutene-2.

* * * * *